US010927143B2

(12) United States Patent
Cozzari et al.

(10) Patent No.: US 10,927,143 B2
(45) Date of Patent: Feb. 23, 2021

(54) METHOD FOR DECONTAMINATING A BIOLOGICAL MATERIAL BY PARTITIONING AND INACTIVATION

(71) Applicant: ALTERGON S.A., Lugano (CH)

(72) Inventors: Costantino Cozzari, Lugano (CH); Luca Angiolini, Lugano (CH)

(73) Assignee: ALTERGON S.A., Lugano (CH)

( * ) Notice: Subject to any disclaimer, the term of this patent is extended or adjusted under 35 U.S.C. 154(b) by 136 days.

(21) Appl. No.: 16/301,923

(22) PCT Filed: Jul. 25, 2017

(86) PCT No.: PCT/EP2017/068722
§ 371 (c)(1),
(2) Date: Nov. 15, 2018

(87) PCT Pub. No.: WO2018/019811
PCT Pub. Date: Feb. 1, 2018

(65) Prior Publication Data

US 2019/0153026 A1 May 23, 2019

(30) Foreign Application Priority Data

Jul. 28, 2016 (IT) ........................ 102016000079328

(51) Int. Cl.
| | |
|---|---|
| *C07K 1/14* | (2006.01) |
| *A61L 2/00* | (2006.01) |
| *B01D 11/04* | (2006.01) |
| *C07K 14/59* | (2006.01) |
| *C12N 9/00* | (2006.01) |
| *A61M 1/36* | (2006.01) |

(52) U.S. Cl.
CPC .............. *C07K 1/14* (2013.01); *A61L 2/0011* (2013.01); *A61L 2/0088* (2013.01); *A61M 1/3695* (2014.02); *B01D 11/0492* (2013.01); *C07K 14/59* (2013.01); *C12N 9/00* (2013.01); *A61L 2202/15* (2013.01); *B01D 11/04* (2013.01); *B01D 2221/10* (2013.01)

(58) Field of Classification Search
CPC ......... C07K 1/14; C07K 14/59; A61L 2/0088; A61L 2/0011; A61L 2202/15; B01D 11/0492; B01D 11/04; B01D 2221/10; C12N 9/00; A61M 1/3695
See application file for complete search history.

(56) References Cited

U.S. PATENT DOCUMENTS

| | | | | | |
|---|---|---|---|---|---|
| 4,201,770 | A * | 5/1980 | Stevens | A61K 39/0006 | 424/185.1 |
| 4,868,130 | A * | 9/1989 | Hargreaves | G01N 33/537 | 436/526 |
| 4,888,427 | A * | 12/1989 | Bodor | C07K 5/06026 | 546/316 |
| 9,458,190 | B2 * | 10/2016 | Lazarev | B01D 11/0288 | |
| 2005/0250935 | A1 | 11/2005 | Dattilo | | |

FOREIGN PATENT DOCUMENTS

WO 2009063065 A1 5/2009

OTHER PUBLICATIONS

Chen 2006 "correlation and prediction of drug molecule solubility in mixed solvent systems with the Nonrandom Two-Liquid Segment Activity Coefficient (NRTL-SAC) model". Ind. Eng. Chem. Res. 2006, 45, 4816-4824. (Year: 2006).*
International Search Report and Written Opinion for Corresponding International Application No. PCT/EP2017/068722 (9 Pages) (dated Nov. 28, 2017).

* cited by examiner

*Primary Examiner* — Liam Royce
(74) *Attorney, Agent, or Firm* — Lucas & Mercanti, LLP

(57) ABSTRACT

The invention relates to a process for decontaminating a biological material by partitioning and inactivation techniques. The process includes the formation of a three-layer liquid system (a-b-c), where the layers are placed one onto the other and are different from each other in density and/or miscibility properties. The upper layer (a) has an aqueous solution of the biological material to decontaminate; the lower layer (c) has the solution inactivating viruses, prions or bacteria; the intermediate layer (b), interposed between the upper and lower layers, separates and protects the biological material from the inactivating solution which has an organic solvent or a mixture of more such solvents, immiscible at least with the upper layer. Moreover, the invention provides specific indications about the density difference between the layers in order to preserve system stability and, at the same time, protect the efficiency of decontamination and the biological activity of the material undergoing decontamination.

12 Claims, No Drawings

METHOD FOR DECONTAMINATING A BIOLOGICAL MATERIAL BY PARTITIONING AND INACTIVATION

CROSS-REFERENCE TO RELATED APPLICATIONS

This application is a 371 of PCT/EP2017/068722, filed Jul. 25, 2017, which claims the benefit of Italian Patent Application No. 102016000079328, filed Jul. 28, 2016.

FIELD OF APPLICATION

The present invention relates to the field of decontamination of biological materials. It describes a new process for inactivating biological materials, in particular of viral, bacterial or prion form, based on partitioning and inactivation principles.

PRIOR ART

It is well known that decontamination, particularly from virus and bacteria or prions, represents a main problem for disinfection of biological materials. This problem occurs particularly, but not exclusively, in the final steps of the industrial processes of purification of target molecules from blood, urine or culture media. In fact, the susceptibility of target molecules of biological origin to chemical or physical treatments does not generally allow to use harsh disinfection procedures, due to the risk of damaging the target molecule or of reducing its activity to very low levels. In particular, it is well known that infection by viruses without envelope (non-enveloped) and by prions represents a difficult problem to solve. In case of viral contaminants, there are several decontamination procedures: they are usually distinguished as inactivation or partitioning procedures. Examples of viral inactivation procedures are heat treatments (for example pasteurization, lyophilization, dry heat use), use of solvents as detergents, and treatment at very low or high pH. Examples of viral partitioning procedures are precipitation processes (for example in ethanol, polyethylene glycol), chromatography (ion exchange, affinity, hydrophobic interaction, reversed-phase) and nanofiltration.

Appropriate validation studies must be performed in order to prove decontamination efficiency of a purification procedure: these studies require adding a known amount of infectious agent to the material at the beginning of the procedure (so called "spiking") and detecting the presence of residual amount of such agent at the end of the procedure; the amount of added infectious agent is measured on a $\log_{10}$ scale and the purification efficiency is expressed as logarithmic reduction factor for the pathogen. Ideally, for regulatory purposes, a purification procedure should show a viral decontamination efficacy of at least 12-15 $\log_{10}$. Such efficacy should be based on various purification steps based on different principles. However, in several purification processes, it is difficult to obtain such result because of the limited applicability of the above-mentioned procedures on industrial scale or because of their harshness toward the target material.

It is even more difficult to eliminate prion contamination, which is less documented and has recently raised concerns about biosafety.

Indeed, due to their nature and small size, prions escape from many partitioning processes which are effective on viruses and their inactivation is difficult to obtain. Exposure to highly alkaline solutions and urea-induced denaturation are among the procedures known to induce substantial prion inactivation. Such procedures often damage the target material and are difficult to apply at the industrial level.

The patent application EP-A-1 593 688 describes a procedure which is a combination between biological material partitioning and inactivation: in an ultracentrifuge tube solutions with decreasing density are stratified: high density urea (inactivating lower phase), sucrose (intermediate phase or "cushion") and solution of biological material to purify (upper phase); the tube is centrifuged, the particulate contaminant material, present in the upper phase, migrates through the intermediate phase and reaches the lower phase, where it is inactivated; the upper phase decontaminated in this way is finally collected as centrifugation supernatant. This procedure provides the advantage of combining two different decontamination methods (partitioning and inactivation); however it proved difficult to apply in the practice and with limited efficiency, especially on an industrial level: in fact the liquid system consisting of the three layers of miscible aqueous solutions separated only by means of different densities is quite unstable, being difficult to realize/maintain and prone to perturbation following a slight handling of the tube; when developed on an industrial scale, it implies discarding many tubes with unsatisfying stratification; in alternative, filling must be performed very slowly and also acceleration and deceleration conditions of the centrifugation process must be chosen carefully in order to avoid to perturb stratification.

Vice versa, total elimination of the intermediate layer could originate a simpler bilayer system, with two solutions being better differentiable on basis of their density, globally improving system stability; however in this case there would be direct contact between the biological material and the denaturing solution, so that the possible yield increase connected to the higher stability of the bilayer system could be jeopardized by an undesired decrease in activity of the biological material.

Finally, it is difficult to search for intermediate phases alternative to sucrose, e.g. capable to form a intermediate phase more discontinuous with the two adjacent phases: in fact the higher discontinuity between the two phases entails the risk to reduce the migration ability of the bacterial/viral/prion material through the different phases, thereby limiting its movement toward the lower inactivating solution; moreover, the search for further substances different from saccharose (e.g. synthesis substances, solvents, etc.) is further limited in view of their possible harmfulness to the stability/activity of the biological material.

In the light of the solutions which are obtained till now and of their limitations, there is thus a significant need for new processes of decontamination of biological material that are easier and quicker to realize, especially on an industrial scale, allowing for efficient decontamination of biological material, avoiding loss of its activity and allowing recovery with high yield.

SUMMARY

The applicant has now provided a new process for decontaminating a biological material which efficiently satisfies the above-mentioned needs.

The process essentially comprises the formation of a three-layer liquid system (a-b-c), where the layers are different from each other in density and/or miscibility properties; the upper layer (a) comprises an aqueous solution of the biological material to decontaminate; the lower layer (c) comprises the solution inactivating said viruses, prions or bacteria; the invention is fundamentally based on the identification of a new intermediate layer (b), interposed between said lower and upper layers, which is able to maximize the stability of the three-layer system in all steps of the decontamination process (i.e. during preparation of the three-layer system, during its transfer into the centrifugation system, during centrifugation, and during the step of collecting protein supernatants) without limiting in any way the migration of the contaminant toward the lower layer, and without damaging the stability of the biological material object of the process. In the process of the invention, the three above-mentioned layers have different densities, in the order (a)<(b)<(c); the intermediate layer is made of an organic solvent (or of a mixture thereof), immiscible at least with the upper layer.

The invention encompasses the use of some preferred organic solvents, advantageously usable within specific volumetric proportions. The invention also provides specific indication about the density difference between the layers, in particular between layers (a) and (b), useful to preserve system stability and at the same time protect decontamination efficiency and biologic activity of the material object of the decontamination.

DETAILED DESCRIPTION

According to the present invention, the term "partitioning" refers to the separation of a particulate element (contaminant agent) from a liquid phase (solution of biological material) that contains it. The term "inactivation" refers to the reduction or the elimination of the activity of said contaminant agents.

According to the present invention, the term "immiscible", referred to the immiscibility between two liquid layers, is intended in the broad sense to define liquid layers that, due to a different extent of hydro/lipophilic properties, density and/or surface tension, always maintain a clear phase separation (at room temperature and pressure and under rest conditions): when possibly subjected to mechanical solicitations (shaking, stirring, centrifugation, etc.) such layers do not permanently homogenize with each other but completely form again the original separation and bi-phasic stratification after appropriate resting time.

The term "partially miscible", referred to miscibility two or more liquid layers, is herein intended to define layers that, due to similar extent of hydro/lipophilic properties, density and/or surface tension, do not show a clear phase separation (at room temperature and pressure and under rest conditions): when possibly subjected to physical or mechanical solicitations (shaking, stirring, centrifugation, etc.) such layers partially homogenize with each other in a stable way, such that even after appropriate resting time the original separation and stratification do not re-form, at least not completely, namely the two phases remain partially mixed and/or interpenetrated.

The biological material which can be used in the present process does not present any limitations from the point of view of the chemical structure and/or biological activity. The only limitation is that it must be soluble (or made soluble by mean of appropriate excipients) in water or aqueous solution: this is essential since the present partitioning process is based on the separability of particulate contaminants (viruses, prions or bacteria), precipitable by centrifugation from the biological material dissolved in solution, the latter being recoverable as supernatant. Biological materials of particular interest are those belonging to one or more of the classes of amino acids, proteins, enzymes hormones, cytokines, co-factors, vitamins, chemical mediators, etc. Preferred examples of such materials are FSH, LH, hCG, testosterone, progesterone, estradiol, T3 and/or T4 thyroid hormone, insulin, glucagon, gastrin, somatostatin, somatotropin, growth hormone, prolactin, renin, angiotensinogen, angiotensin, gonadotropin, cortisol, adrenocorticotropic hormone (ACTH), modified amino acids, L-DOPA, dopamine, epinephrine, norepinephrine, serotonin, histamine, GABA, their derivatives, etc. Particularly preferred biological materials are follicle-stimulating hormone (FSH), luteinizing hormone (LH), human chorionic gonadotropin (hCG), thyroid hormones, i.e. triiodothyronine (T3) and/or thyroxine (T4), progesterone, testosterone, and derivatives thereof. The biological material can also be a physiological liquid containing target molecules which are dissolved or soluble in it, which are meant to be separated from the particulate; examples of physiological liquids are blood, plasma, urine, amniotic fluid, cerebrospinal fluid, etc.

Contaminants which in the present process are separable from the biological materials are particulate contaminant, typically viruses, prions or bacteria. The term "contaminant" however encompass any other particulate possibly associated to the biological material, even if not toxic for humans or animals (for examples materials in suspension, powders, etc.); such particulates are in any case undesired since, if they are contained in the final biological product, they reduce its titer.

The upper layer (a) used in the present invention comprises an aqueous solution of the chosen biological material. Depending on the degree of solubility in water of said materials, the solution constituting the layer (a) could possibly contain solubilizing excipients; further examples of excipients that can be used are buffering agents and tonicity-adjusting agents, useful to optimize condition of conservation in solution of the chosen biological material; such excipients, merely discretionary, are in no way essential to stabilize the biological material with respect to its contact with the intermediate layer (b); it was indeed experimentally verified by the Applicant that the intermediate layer realized according to the present invention does not in any way modify the activity of the biological material in the adjacent layer (a). Ionic substances such as for example sodium chloride or glycerol can be used as density adjusting agent.

Layer (a) is the one with lowest density, thus being stratifiable on the upper surface of the multi-layered system; without prejudice to this condition, no absolute density values are required for this layer; however, being aqueous solutions, the density will often be similar or slightly higher than the one of water; indicative reference values for the density of layer (a) are between 1.001 and 1.050; higher values are possible, depending on the type of biological material (e.g. physiological liquid) used.

The intermediate layer (b) comprises an organic solvent, or more than one (intermixable) organic solvents mixed with each other; such solvents (or mixtures thereof) must be immiscible with the aqueous solution of layer (a) and also display a density intermediate between those of layers (a) and (c), so as to allow the appropriate intermediate stratification. Advantageously, the density of layer (b) is at least 0.025 mg/mL higher than the one of layer (a); it was in fact experimentally verified by the Applicant that such density difference is sufficient to guarantee a stable separation of layer (a) from the remaining layers of the three-layer system; in contrast there is no specific upper limit to the density difference between layers (a) and (b), considering that the higher is the density difference, the more stable is the system during the various steps of the process; a useful upper reference value for the above-mentioned density difference is of about 0.3 mg/mL. Consequently, the density difference between layers (a) and (b) preferably ranges between 0.030 and 0.3 mg/mL. It is understood that the maximum value of density chosen for layer (b) should always be lower than the one chosen for layer (c). Without prejudice to the above conditions, non-limiting reference density ranges (absolute values) for layer (b) are between 1.07 and 1.20.

Compared to the use of single solvents, the use of a mixture of solvents in layer (b) provides the advantage of an easier modulation of the density characteristics. Convenient results can be obtained mixing an organic solvent with high density with an organic solvent with low density in appropriate proportions to obtain a density being intermediate with respect to the inactivating solution and the solution to decontaminate. Preferably it is possible to use, as constituent of layer (b), a mixture of a halogenated aliphatic organic solvent with an aromatic organic solvent, such solvents being present in the respective volumetric proportions between 1:0.5 and 1:4, or preferably between 1:0.8 and 1:3. Preferred examples of halogenated aliphatic organic solvents are: methyl chloride, methylene chloride, chloroform, carbon tetrachloride; preferred examples of aromatic organic solvents are benzene, toluene, $C_{2-4}$ alkyl benzene (for example ethylbenzene, propylbenzene and their isomers), xylene and their derivatives. Particularly preferred solvents are chloroform and toluene; non-limiting examples of mixtures thereof are those realized in the proportions 1:1, 1:1.5 e 1:2.

The Applicant also verified if the contact between phase (a) and the organic solvents of phase (b) could entail a partial denaturation of the biological material, with possible undesired reduction of its activity. Such tests gave completely negative results, showing that phase (b), although very different from phase (a) (being optimized for the conservation of the biological) does not in any way jeopardize the activity of such material.

The lower layer (c) comprises a solution with higher density than those of layers (a) and (b); it comprises a substance able to inactivate the viral, prion or bacterial particulate that, following centrifugation, comes into contact with this layer. There is no limitation to the choice of the inactivating substance: it can be conveniently chosen among those known for use in decontamination processes by inactivation; advantageously is the used substance also confers to layer (c) the desired density: examples of such substances are highly concentrated urea solutions, or highly concentrated solutions of an alkaline hydroxide such as for example NaOH. Preferred examples are urea solutions having a concentration of at least 6M and pH of at least 8.0, or of alkaline hydroxide having a concentration of at least 0.5 M; there are no maximum limitations to the concentration or the pH for such solutions, considering that each concentration (or alkalinity) increase further enhances the inactivating power of layer (c); however useful ranges for the urea solution are between 7M and 9M, with pH between 8.0 and 11.0, preferably equal to 9.5; useful ranges for the NaOH solution are between 1M and 2M. The inactivating solutions, e.g. urea solution, can comprise a suitable buffering agent, e.g. Tris-Cl to maintain pH in the desired range; they can moreover comprise suitable agents which interfere with disulphide bridges (e.g. dithiothreitol), so as to facilitate denaturation of the protein component of the contaminants. Density adjusting agents, e.g. NaCl, NaBr, NaI (sodium iodide) or glycerol can be possibly used (as well as in the phases (a) and/or (b) wherever desired).

Differently from the interface between layers (a) and (b), the interface between layers (b) and (c) does not have a particular criticality, namely it is not required that the layers (b) and (c) have strongly different densities; according to the invention it is in fact sufficient to realize a minimal separation between the phases constituting layers (b) and (c); such scarce separation is not a drawback but rather a further advantage: in fact it facilitates the migration, during centrifugation, of the viral, prion or bacterial particulate from the intermediate layer (b) toward the layer (c) where the inactivation reaction takes place. A possible partial mixing of phases (b) and (c) following centrifugation, even if permanent, does not constitute a problem for the invention since such phases represent the process waste; vice versa, the decontaminated biological material remains in layer (a): the latter remains permanently separated after centrifugation and it is easily collected as supernatant upper phase; a possible undesired flowing back of the contaminant material toward layer (a) is also prevented by the difference in miscibility/density imposed between layer (a) and the remaining two layers.

Without prejudice to the above-mentioned conditions, non-limiting reference density (absolute values) ranges for layer (c) are between 1.08 and 1.30.

The partitioning/inactivation process is performed through the following steps:

(i) in an ultracentrifuge tube, progressively stratify layers (c), (b), (a);
(ii) centrifuge the tube prepared in (i);
(iii) collect layer (a) as centrifugation supernatant, containing the decontaminated biological material.

The steps (i) and (iii) are conveniently performed using a syringe or an equivalent device for filling/aspiration, preferably developed for use on industrial scale. Ultracentrifuge tubes can be chosen among those commercially available, with preference for those with internal surfaces which are inert to organic solvents, e.g. teflon internal surfaces. Step (ii) is performed by centrifuging within broad ranges of G and time length values (typically a range between 50.000 and 70.000 G, for time length between 30 minutes and 2 hours); deviations from these values are possible depending on the specific characteristics of the used biological material its presumable contaminant load. During ultracentrifugation particulate contaminants contained in the biological product and originally present in the solution of layer (a), due to their mass, are attracted to the bottom of the tube, i.e. they pass through layer (b) and concentrate in layer (c), where they are inactivated by contact with the inactivating solution therein contained; depending on the used centrifugation conditions, the contaminants can remain suspended in layer (c) or concentrate as precipitate or pellet on the bottom of the tube. The decontamination process ends with the aspiration of the centrifugation supernatant containing the solution of the decontaminated biological product; it can then be conserved in form of solution, liquid or frozen, or it can be recovered in solid form upon removal of the liquid phase; for this purpose milder procedures are used (e.g. lyophilization or slow evaporation) to preserve the activity of the biological product; more rapid/drastic conditions, e.g. boiling, can be used in case of biological products which are sufficiently stable.

In summary, the present invention has allowed to significantly improve the known partitioning and inactivation processes, resulting in a process which is easy to implement on an industrial scale, with high productive yield and which strongly preserves the biological activity of the material to decontaminate. In particular, the intermediate layer with the characteristics described for the invention allowed to realize a particularly stable layered triphasic system, which does not in any way hinder the migration of the viral, prion or bacterial particulate toward the lower phase during centrifugation; in particular, due to the characteristics of non-miscibility of the intermediate phase, this can have a density just slightly higher than the density of the upper layer containing the product, which leads to a much easier migration of the bacterial/viral/prion particles toward the underlying inactivating phase; the intermediate layer itself, albeit highly dissimilar from the solution of biological material, does not damage the biological activity of the latter.

The invention is now described by way of the following non-limiting examples.

EXAMPLES

Example 1: Preparation of the Inactivating Phase (Layer (c))

Urea-based and NaOH-based inactivating solutions were prepared.

The urea solutions further comprised a 0.5M Tris-Cl buffer at 9.5 pH, dithiothreitol (DTT, conc. 10 mM) and possibly NaBr as density adjusting agent.

The NaOH solutions were realized using 1M NaOH and glycerol as density adjusting agent.

TABLE 1

Inactivating solutions

| Solution | Density at 20° C. |
|---|---|
| 8M Urea, 0.5M Tris-Cl 10 mM DTT pH 9.5 | 1.1407 |
| 8M Urea, 0.5M Tris-Cl, 10 mM DTT, 1M NaBr pH 9.5 | 1.2174 |
| 8M Urea, 0.5M Tris-Cl, 10 mM DTT, 1.2M NaBr pH 9.5 | 1.2283 |
| 8M Urea, 0.5M Tris-Cl, 10 mM DTT, 1.5M NaBr pH 9.5 | 1.2514 |
| 8M Urea, 0.5M Tris-Cl, 10 mM DTT, 1.7M NaBr pH 9.5 | 1.2637 |
| 8M Urea, 0.5M Tris-Cl, 10 mM DTT, 2M NaBr pH 9.5 | 1.2903 |
| 1M NaOH in 25% (v/v) Glycerol | 1.095 |
| 1M NaOH in 30% (v/v) Glycerol | 1.11 |
| 1M NaOH in 40% (v/v) Glycerol | 1.1395 |

Example 2: Preparation of the Intermediate Phase (Layer (b)

Chloroform-based and toluene-based solutions, in proportions 1:1, 1:1.5 and 1:2, were prepared.

TABLE 2

Intermediate solutions

| Solution | Density at 20° C. |
|---|---|
| Chloroform | 1.46 |
| Toluene | 0.863 |
| Chloroform:Toluene = 1:1 | 1.178 |
| Chloroform:Toluene = 1:1.5 | 1.116 |
| Chloroform:Toluene = 1:2 | 1.074 |

Chloroform boiling point 61° C.

Toluene boiling point 110° C.

As reference, intermediate aqueous solutions based on sucrose aqueous solutions were prepared, following prior art references (EP 1 593 688).

TABLE 3

Intermediate solutions with sucrose (reference)

| Solution | Density at 10° C. | Density at 20° C. |
|---|---|---|
| 10% w/v sucrose in water | 1.041 | 1.038 |
| 20% w/v sucrose in water | 1.085 | 1.081 |
| 30% w/v sucrose in water | 1.133 | 1.127 |
| 40% w/v sucrose in water | 1.183 | 1.176 |

The modulation of the density required the use of massive amount of sucrose, thereby obtaining highly concentrated solutions, unsuitable for the contact with solutions comprising molecules of biological interest.

Example 3: Preparation of the Solution of Biological Material (Layer (a))

Bovine serum albumin (BSA) solutions, at concentrations between 5 and 20 mg/mL, with or without NaCl were prepared as reference biological material. The obtained solutions had the following characteristics.

TABLE 4

Protein solutions

| Solution | Density at 20° C. |
|---|---|
| BSA 5 mg/ml in water | 1.001 |
| BSA 10 mg/ml in water | 1.002 |
| BSA 20 mg/ml in water | 1.005 |
| BSA 5 mg/ml in 1M NaCl | 1.043 |
| BSA 10 mg/ml in 1M NaCl | 1.045 |
| BSA 20 mg/ml in 1M NaCl | 1.045 |
| BSA 5 mg/ml in 2M NaCl | 1.079 |
| BSA 10 mg/ml in 2M NaCl | 1.081 |
| BSA 20 mg/ml in 2M NaCl | 1.081 |

The easiness of stratification of the obtained solutions on the solutions of layer (b) described in the previous example was then verified.

TABLE 5

Test of stratification between protein solution and intermediate solution

| Intermediate solution | Protein sol. compos. | Aspect after centrifugation |
|---|---|---|
| Chlorof:Toluene = 1:1 | 20 mg/ml BSA in water | OK |
| Chlorof:Toluene = 1:1 | 20 mg/ml BSA in 2M NaCl | OK |
| Chlorof:Toluene = 1:1.5 | 20 mg/ml BSA in water | OK |
| Chlorof:Toluene = 1:1.5 | 20 mg/ml BSA in 2M NaCl | OK |
| Chlorof:Toluene = 1:1.5 | 20 mg/ml BSA in 1M NaCl | OK |
| Chlorof:Toluene = 1:2 | 20 mg/ml BSA in 2M NaCl | NO |
| Chlorof:Toluene = 1:2 | 20 mg/ml BSA in 1M NaCl | OK |
| Chlorof:Toluene = 1:2 | 20 mg/ml BSA in 0.1M Na Phosphate, 1M NaCl pH 7.2 | OK |
| Chlorof:Toluene = 1:2 | 20 mg/ml BSA in 0.1M Na Phosphate, 0.5M NaCl pH 7.2 | OK |

OK = subdivision as desired
NO = the protein solution is thicker than the intermediate phase and sinks.

TABLE 6

Test of stratification between intermediate solution and inactivating solution

| Inactivating solution | Intermediate solution | Aspect after centrifugation |
|---|---|---|
| 1M NaOH in 25% (v/v) Glycerol | Chlorof:Toluene = 1:1 | NO |
| 1M NaOH in 25% (v/v) Glycerol | Chlorof:Toluene = 1:1.5 | NO |
| 1M NaOH in 25% (v/v) Glycerol | Chlorof:Toluene = 1:2 | OK |
| 1M NaOH in 30% (v/v) Glycerol | Chlorof:Toluene = 1:1 | NO |
| 1M NaOH in 30% (v/v) Glycerol | Chlorof:Toluene = 1:1.5 | NO |
| 1M NaOH in 30% (v/v) Glycerol | Chlorof:Toluene = 1:2 | OK |
| 1M NaOH in 40% % (v/v) Glycerol | Chlorof:Toluene = 1:1 | NO |
| 1M NaOH in 40% % (v/v) Glycerol | Chlorof:Toluene = 1:1.5 | OK |
| 1M NaOH in 40% % (v/v) Glycerol | Chlorof:Toluene = 1:2 | OK |
| 8M Urea, 0.5M Tris-Cl 10 mM DTT pH 9.5 | Chlorof:Toluene = 1:1 | NO |
| 8M Urea, 0.5M Tris-Cl 10 mM DTT pH 9.5 | Chlorof:Toluene = 1:1.5 | OK |
| 8M Urea, 0.5M Tris-Cl 10 mM DTT pH 9.5 | Chlorof:Toluene = 1:2 | OK |
| 8M Urea, 0.5M Tris-Cl, 10 mM DTT, 1M NaBr pH 9.5 | Chlorof:Toluene = 1:1 | OK |
| 8M Urea, 0.5M Tris-Cl, 10 mM DTT, 1M NaBr pH 9.5 | Chlorof:Toluene = 1:1.5 | OK |
| 8M Urea, 0.5M Tris-Cl, 10 mM DTT, 1M NaBr pH 9.5 | Chlorof:Toluene = 1:2 | OK |

Example 4 Test of Biological Activity

To verify if a prolonged interface contact between the protein aqueous phase (a) and the intermediate organic phase (b) could jeopardize the activity of FSH, various small tubes were prepared with the intermediate solution (b), upon which the different FSH solutions were stratified. Samples were incubated in the refrigerator for 18 h and subsequently their FSH activity was determined in comparison to the initial activity of each solution. The detail of the solutions and the recovery of FSH is shown in the following table.

TABLE 7

Evaluation of FSH activity after 18 hours contact with the organic phase of chloroform/toluene

| Intermediate organic phase | Composition of the FSH solution | % FSH recovered after 18 h contact with the organic phase |
|---|---|---|
| Chloroform:Toluene = 1:1 | 60 U/ml FSH in water | 126% |
| Chloroform:Toluene = 1:1 | 60 U/ml FSH in 1M NaCl | 95% |
| Chloroform:Toluene = 1:1 | 60 U/ml FSH in 2M NaCl | 98% |
| Chloroform:Toluene = 1:1 | 60 U/ml FSH, 10 mg/ml BSA | 99% |
| Chloroform:Toluene = 1:1 | 60 U/ml FSH, 10 mg/ml BSA, 1M NaCl | 102% |
| Chloroform:Toluene = 1:1 | 60 U/ml FSH, 10 mg/ml BSA, 2M NaCl | 102% |
| Cloroform:Toluene = 1:1.5 | 60 U/ml FSH in water | 100% |
| Chloroform:Toluene = 1:1.5 | 60 U/ml FSH in 1M NaCl | 100% |
| Chloroform:Toluene = 1:1.5 | 60 U/ml FSH, 10 mg/ml BSA | 104% |
| Chloroform:Toluene = 1:1.5 | 60 U/ml FSH, 10 mg/ml BSA, 1M NaCl | 101% |
| Chloroform:Toluene = 1:2 | 60 U/ ml FSH in water | 98% |
| Chloroform:Toluene = 1:2 | 60 U/ml FSH in 1M NaCl | 97% |
| Chloroform:Toluene = 1:2 | 60 U/ml FSH, 10 mg/ml BSA | 108% |
| Chloroform:Toluene = 1:2 | 60 U/ml FSH, 10 mg/ml BSA, 1M NaCl | 106% |

Abbreviations:
NaOH: = Sodium hydroxide;
NaCl = Sodium chloride;
NaBr = Sodium bromide;
DTT = dithiothreitol;
Tris = tris(hydroxymethyl)aminomethane;
BSA = bovine serum albumin.

From the above-shown table it is possible to note that FSH was not damaged (±variations by a few percentage units are intrinsic in the type of performed test).

The invention claimed is:

1. A process for decontaminating a biological material from viral, prion and/or bacterial contaminants, comprising centrifuging a three-layer liquid system comprising:
   (a) an upper layer comprising an aqueous solution of the biological material to decontaminate;
   (b) an intermediate layer comprising one or more organic solvents; and
   (c) a lower layer comprising an inactivating solution for said contaminants;
   wherein said layers have different densities, in the order: (a)<(b)<(c), and wherein the intermediate layer (b) is a mixture of a halogenated aliphatic organic solvent with an aromatic organic solvent, in volume proportions of between 1:0.5 and 1:4, and is immiscible with the upper layer (a).

2. The process according to claim 1, wherein the upper and intermediate layers (a) and (b) have a density difference of at least 0.025 g/mL.

3. The process according to claim 1, wherein the upper and intermediate layers (a) and (b) have a density difference of between 0.030 and 0.3 g/mL.

4. The process according to claim 1, wherein the halogenated aliphatic organic solvent is selected from the group consisting of methyl chloride, methylene chloride, chloroform and carbon tetrachloride, and the aromatic organic solvent is selected from the group consisting of toluene, benzene, $C_{2-4}$ alkyl benzene, xylene and derivatives thereof.

5. The process according to claim 1, wherein the intermediate layer (b) is partially miscible with the lower layer (c).

6. The process according to claim 1, wherein the lower layer (c) is a urea solution having concentration of at least 6M, or a solution of an alkaline or alkaline earth metal hydroxide having concentration of at least 0.5 M.

7. The process according to claim 1, wherein the intermediate layer (b) is a mixture of chloroform and toluene and/or the lower layer (c) is selected from the group consisting of: dithiothreitol, urea, sodium bromide, sodium chloride, sodium iodide, an agent that confers to said inactivating solution a pH of between 8 and 11, and mixtures thereof.

8. The process according to claim 1, wherein the biological material is selected from the group consisting of amino acids, proteins, enzymes and hormones.

9. The process according to claim 1, wherein the biological material is selected from the group consisting of follicle stimulating hormone (FSH), luteinizing hormone (LH), human chorionic gonadotropin (hCG), testosterone, progesterone, estradiol, T3 and/or T4 thyroid hormone, insulin, glucagon, gastrin, somatostatin, somatotropin, growth hormone, prolactin, renin, angiotensinogen, angiotensin, gonadotropin, cortisol, adrenocorticotropic hormone (ACTH), L-3,4-dihydroxyphenylalanine (L-DOPA), dopamine, epinephrine, norepinephrine, serotonin, histamine, gamma-aminobutyric acid (GABA) and derivatives thereof.

10. The process according to claim 1, wherein one or more of the following conditions are met:
the upper layer (a) comprises: said biological material at a concentration of between 1 and 100 mg/mL, and a buffering agent which confers to the upper layer (a) a pH of between 6.5 and 8.0;
the intermediate layer (b) is a mixture of chloroform and toluene in volumetric proportions of between 1:0.5 and 1:4; and
the lower layer (c) is a urea solution having a molarity of between 7M and 9M, comprising dithiothreitol, NaBr, and a buffering agent which confers to the lower layer (c) a pH of between 8.0 and 11.0.

11. The process according to claim 10, where one or more of the following conditions are met:
the upper layer (a) comprises: said biological material at a concentration of between 10 and 50 mg/mL, a buffering agent which confers to the upper layer (a) a pH of between 7 and 7.5;
the intermediate layer (b) is a mixture of chloroform and toluene in volumetric proportions of between 1:0.8 and 1:3;
the lower layer (c) is a 8M urea solution, comprising dithiothreitol, NaBr, and a buffering agent which confers to the lower layer (c) a pH of between 8.0 and 11.0.

12. The process according to claim 1, wherein the intermediate layer (b) is a mixture of a halogenated aliphatic organic solvent with an aromatic organic solvent, in volume proportions of between 1:0.8 and 1:3.

\* \* \* \* \*